United States Patent [19]

Carter

[11] Patent Number: 5,409,652
[45] Date of Patent: Apr. 25, 1995

[54] METHOD OF MAKING MEDICO-SURGICAL DEVICES

[75] Inventor: Roland H. C. Carter, Hythe, England

[73] Assignee: Smiths Industries Public Limited Company, London, England

[21] Appl. No.: 75,417

[22] Filed: Jun. 14, 1993

[30] Foreign Application Priority Data

Jun. 24, 1992 [GB] United Kingdom ............... 9213379

[51] Int. Cl.6 .................................................. B29C 43/00
[52] U.S. Cl. ...................................... 264/105; 264/263; 29/854; 29/855; 128/642; 607/122
[58] Field of Search ............... 128/642; 607/122–126; 29/854, 855; 264/104, 105, 263

[56] References Cited

U.S. PATENT DOCUMENTS

| | | | |
|---|---|---|---|
| 3,959,429 | 5/1976 | Benning | 264/263 X |
| 4,073,287 | 2/1978 | Bradley et al. | 128/642 |
| 5,029,585 | 7/1991 | Lieber et al. | 128/642 |

FOREIGN PATENT DOCUMENTS

| | | | |
|---|---|---|---|
| 101595 | 2/1984 | European Pat. Off. | 128/642 |
| 2135196 | 8/1984 | United Kingdom . | |
| 978826 | 11/1982 | U.S.S.R. | 128/642 |

*Primary Examiner*—Lee S. Cohen
*Attorney, Agent, or Firm*—Pollock, VandeSande and Priddy

[57] ABSTRACT

A catheter has a tubular plastics body and an insulated metal wire extending along the bore of the catheter through an aperture close to its patient end. The exposed end of the wire is covered by and connects with an electrically-conductive plastics material injection molded about the tubular body to form an electrode with a convex surface projecting from the surface of the catheter.

3 Claims, 1 Drawing Sheet

METHOD OF MAKING MEDICO-SURGICAL DEVICES

BACKGROUND OF THE INVENTION

This invention relates to medico-surgical devices.

The invention is more particularly concerned with medico-surgical catheters or probes having electrodes.

Conventionally, medico-surgical catheters provided with an electrode have a metal wire extending along the catheter which is insulated along its length such as by the material of the catheter along which it extends. The electrode may be formed by a separate metal member welded or soldered to the wire and is located on the surface of the catheter where it is exposed for contact with adjacent tissue. Examples of such devices are described in EP 0366127, U.S. Pat. No. 3,951,136, EP 0334086 and WO 92/17150.

There are several problems with using metal electrodes. Many metals suitable for use as electrodes are not very biocompatible. Although in some circumstances they can be used satisfactorily, where the electrode has to have a large surface area or is inserted in the body for prolonged periods, it can lead to adverse reactions. Inert metals which are biocompatible, such as gold or platinum, are expensive and, therefore, only suitable for use on reusable catheters. Because of the risk of cross infection, it is preferable in most circumstances to use disposable, single-use catheters which must be of low cost. Also, it is often desired for the main body of the catheter to be of a plastics material because of its flexibility and softness but these plastics materials are often unsuitable for the repeated sterilization required in reusable catheters.

Another problem with using metal electrodes on a plastic catheter, probe or similar body is the difficulty of providing a secure mount. The difference between the physical properties of metal and plastics increases the risk that the electrode will separate from the body on flexing or other deformation. In medical applications, it is clearly very important that there is no risk of the electrode coming away from the catheter or of damaging the catheter itself in such a way that a part of the catheter becomes detached. Furthermore, it can be difficult to assembly a metal electrode into a plastics body without damaging the plastics body. Where it is desired to produce a flexible catheter or probe with an electrode, the hard, rigid nature of metal materials can compromise the overall flexibility of the catheter.

BRIEF SUMMARY OF THE INVENTION

It is an object of the present invention to provide a medico-surgical device including an electrode and a method of making a device that can be used to alleviate these problems.

According to one aspect of the present invention there is provided a medico-surgical device including an elongate plastics body, an electrically-conductive member extending along the body and insulated along a major part of its length from the exterior of the body, and an electrode member exposed to the exterior of the body so as to make contact with patient tissue, the electrode member being formed of an electrically-conductive plastics material moulded onto the body making electrical contact with the conductive member.

The electrode member is preferably injection moulded onto the body. The electrode member preferably projects above the surface of the body and may have a convex surface. The electrically-conductive member may be a metal wire such as an insulated wire. The plastics body may be a catheter with a bore extending along its length, the electrically-conductive member extending along the bore. The electrically-conductive plastics material may be a plastics material loaded with carbon.

According to another aspect of the present invention there is provided a method of making a medico-surgical device comprising the steps of providing an elongate plastics body having an electrically-conductive member extending along its length, the member being insulated from the exterior of the body along a major part of its length and exposed at its patient end, and moulding onto the body over the exposed end of the electrically-conductive member an electrode of an electrically-conductive plastics material so that the electrode bonds securely with the body and is electrically connected with the electrically-conductive member.

A monitoring catheter and its method of manufacture, in accordance with the present invention, will now be described, by way of example, with reference to the accompanying drawings.

DETAILED DESCRIPTION OF THE PREFERRED EMBODIMENT

Figure 1:
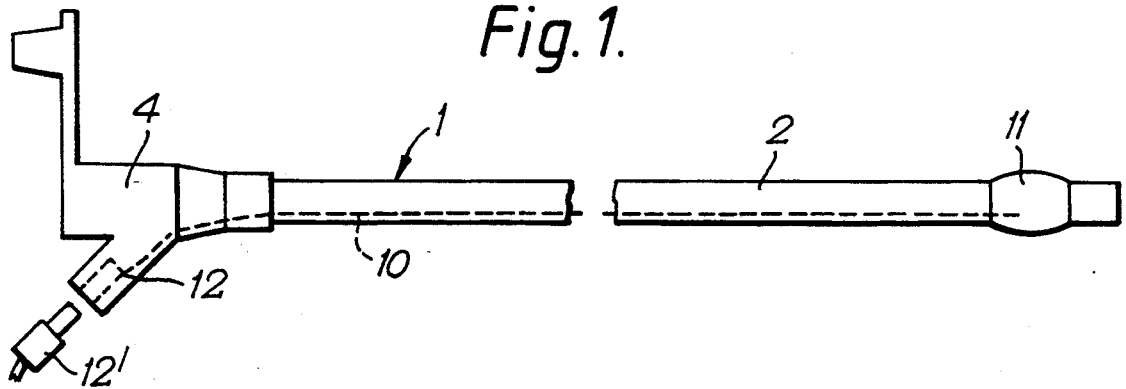
FIG. 1 is a side elevation view of the catheter.
Figure 2:
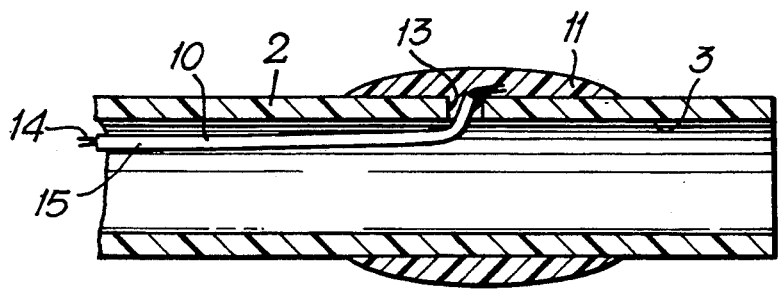
FIG. 2 is a sectional side elevation view of the patient end of the catheter to an enlarged scale.

With reference first to FIGS. 1 and 2, the catheter 1 has a tubular body 2 of a flexible, electrically-insulating plastics material such as PVC which has an internal diameter of 2.4 mm, an external diameter of 3.2 mm and is 75 mm long. A single bore 3 extends along the entire length of the body 2, opening at the patient end and at the machine end of the catheter via a coupling 4.

The catheter 1 also includes an electrically-conductive wire or other elongate element 10 which extends from the machine end coupling 4 to an electrode 11 formed 10 mm from the patient end of the catheter. The wire 10 may extend along the bore 3 of the catheter, as shown, or through a separate lumen formed in the wall of the tubular body 2. In the arrangement illustrated, the machine end of the wire 10 is terminated by an electrical coupling 12 and its other end extends through an aperture 13 in the wall of the tubular body 2 underlying the electrode 11. The wire 10 preferably has a metal core 14 of copper and an insulating plastics sleeve 15 a short length of which is removed from the wire at its patient end. This uninsulated end of the wire 10 projects externally of the aperture 13 and is wrapped close around the outside of the body 2.

The electrode 11 is provided by a conductive plastics material which is moulded into a ring about the circumference of the body 2 about 10 mm from its patient end. The electrode 11 is about 10 mm long and projects above the surface of the body 2 by 2 mm midway along its length. The ends of the electrode 11 are rounded so that it presents a convex surface externally and forms a relatively smooth transition with the body 2. The conductive plastics material from which the electrode 11 is formed comprises PVC or polyurethane loaded with about 30% by weight of carbon. The conductive plastics material is injection moulded around the body 2 in contact with the exposed core 14 of the wire 10 so that the wire is electrically connected to the electrode 11.

In use, the catheter 1 is inserted into a body cavity such as the oesophagus or a blood vessel so that the electrode 11 contacts tissue lining the wall of the cavity. This enables monitoring of electrical activity within that region of the body, for example, ECG monitoring. Alternatively, the catheter can be used to provide electrical stimulation by supplying an electrical signal to the electrode such as, for example, for cardiac pacemaking, electroanalgesia, muscle control and the like.

Figure 3:
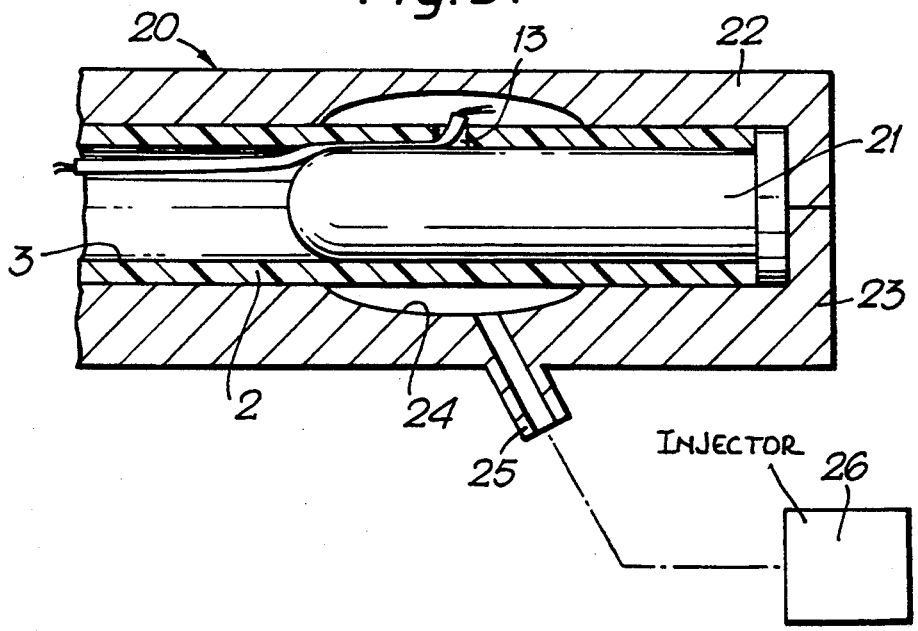
FIG. 3 is a sectional side elevation of the catheter during manufacture.

The catheter 1 is manufactured in the manner shown in FIG. 3. The wire 10 is pushed through the aperture 13 and threaded along the bore 3 until it emerges from the machine end of the body 2, with a short length of uninsulated wire projecting from the aperture. The core 14 of the wire is wrapped around the body 2 and may be held in place by a thin layer of conductive adhesive. As shown in FIG. 3, the body 2 with the wire 10 in place is inserted into a two-part injection moulding cavity 20. Prior to insertion, a metal supporting plug 21 is pushed into the patient end of the body 2. The plug 21 is a close sliding fit within the bore 3 and extends a short distance proximally of the region in which the electrode will be formed. The two parts 22 and 23 of the cavity 20 form together a tubular cavity, for reception of the body 2, and an annular recess 24 which defines the shape of the electrode 11. The recess 24 communicates via a sprue 25 with an injector 26 of molten conductive plastics material.

The temperature of the molten injectate is slightly higher than the melting point of the material of the body 2 so that, as it contacts the surface of the body, it causes some flow of the body material in the immediate vicinity. This causes the two plastics to mix together at the surface of the body 2 and produces a high strength bond between the electrode 11 and the body 2. A part of the injectate also flows into the aperture 13 so as to seal it and further help in anchoring the wire 10 in position. The plug 21 serves the purposes of preventing the body 2 collapsing as a result of the injection pressure, of preventing flow of injectate out of the aperture 13 and of holding the wire 10 in position during moulding. When the recess 24 in the mould cavity 20 has been filled, the two parts 22 and 23 of the cavity are separated and the body, with its electrode moulded in place, is removed.

The completed catheter 1 can be made at low cost because it does not include an expensive metal electrode. Because the material of the electrode is similar to that of the body itself, both materials have similar flexibility, thereby reducing the risk of separation between the electrode and the body. The join between the electrode and the body is of high strength because the two materials bond together. The deformable nature of the electrode reduces the risk of it causing trauma to the patient on insertion. Because the electrode material is biocompatible, the risk of adverse reaction is reduced.

The electrode can be shaped as desired by the shape of the mould cavity so that it protrudes above the surface of the probe and improves contact of the electrode with the adjacent tissue.

Instead of a wire, some other electrically-conductive member could be used to make connection with the electrode. This could take the form of a strip of conductive plastics extruded or painted along the catheter. Alternatively, a lumen extending within the wall of the tube could be filled with a conductive material.

The invention can also be used with other devices such as probes and can be used to provide any number of electrodes. A shallow recess could be formed around the body into which the electrode is moulded. The catheter could be provided with an inflatable cuff.

What I claim is:

1. A method of making a medico-surgical device comprising the steps of: providing an elongate catheter having a bore extending along the length of said catheter and having an electrically-conductive member extending along said length, the member being insulated from an exterior of the catheter along a major part of said length and exposed at a patient end of said catheter; and moulding onto the catheter over the exposed end of the electrically-conductive member an electrode of an electrically-conductive plastics material so that the electrode bonds securely with the catheter and is electrically connected with the electrically-conductive member; said method including the further steps of inserting a removable plug into the bore to extend along a region of the catheter on which the electrode is moulded, and subsequently removing the plug after the moulding step.

2. A method of making a medico-surgical device comprising the steps of providing an elongate plastics body having an electrically-conductive member extending along the length of said body, the member being insulated from an exterior of the body along a major part of said length; forming an opening in a wall of the body through which the electrically-conductive member is exposed at a patient end of said body; inserting the elongate plastics body into a mould cavity, said mould cavity having an internal annular recess of concave shape that is located to overlie said opening; and injecting into the recess an electrically-conductive plastics material to form an electrode of convex shape around the plastics body that projects above an exterior surface of the body, is securely bonded with the body, and is electrically connected with the electrically-conductive member.

3. A method according to claim 2, in which the plastics body is a catheter with a bore extending along the length of said catheter, and wherein the method includes the steps of inserting a removable plug in the bore to extend along a region of the body on which the electrode is moulded and subsequently removing the plug after the moulding step.

* * * * *